(12) United States Patent
Fürtinger

(10) Patent No.: US 8,160,673 B2
(45) Date of Patent: Apr. 17, 2012

(54) MEDICAL ELECTRODE

(75) Inventor: Christian Fürtinger, Innsbruck (AT)

(73) Assignee: Leonh. Lang, Innsbruck (AT)

( * ) Notice: Subject to any disclaimer, the term of this patent is extended or adjusted under 35 U.S.C. 154(b) by 1013 days.

(21) Appl. No.: 11/855,225

(22) Filed: Sep. 14, 2007

(65) Prior Publication Data

US 2008/0071159 A1    Mar. 20, 2008

(30) Foreign Application Priority Data

Sep. 15, 2006    (AT) ................................ A 1542/2006

(51) Int. Cl.
*A61B 5/04*    (2006.01)

(52) U.S. Cl. ......... 600/391; 600/392; 607/152; 607/153

(58) Field of Classification Search .................. 600/391, 600/392, 394; 607/149, 152
See application file for complete search history.

(56) References Cited

U.S. PATENT DOCUMENTS

| | | | |
|---|---|---|---|
| 3,805,769 A * | 4/1974 | Sessions | 600/392 |
| 3,989,035 A * | 11/1976 | Zuehlsdorff | 600/391 |
| 4,029,086 A * | 6/1977 | Corasanti | 600/391 |
| 4,522,211 A | 6/1985 | Bare et al. | |
| 5,632,274 A | 5/1997 | Quedens et al. | |
| 6,743,223 B1 * | 6/2004 | Lang | 606/32 |

FOREIGN PATENT DOCUMENTS

| | | |
|---|---|---|
| EP | 0635239 A1 | 1/1995 |
| WO | WO2006046160 A1 | 5/2006 |

OTHER PUBLICATIONS

European Publication No. 07017727 Search Report dated Dec. 17, 2007.

* cited by examiner

*Primary Examiner* — Lee Cohen
(74) *Attorney, Agent, or Firm* — Rissman Hendricks & Oliverio LLP

(57) ABSTRACT

A medical electrode for bonding to the skin of a patient comprises a support which adheres to the skin and a holding element for at least one electrically conducting connection piece, wherein the skin side of the connection piece is covered with an electrically conducting gel, in particular in a sponge, wherein the gap on the skin side between the holding element and the electrically conducting connection piece is closed by a sealing element which is preferably ring-like.

5 Claims, 2 Drawing Sheets

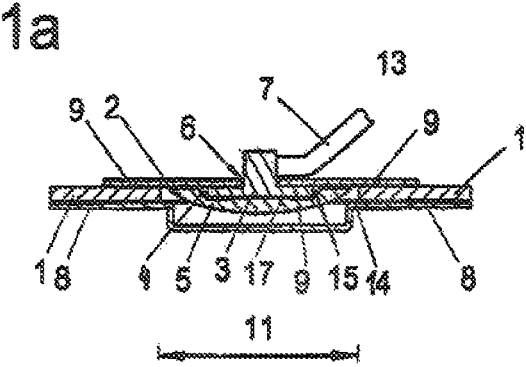
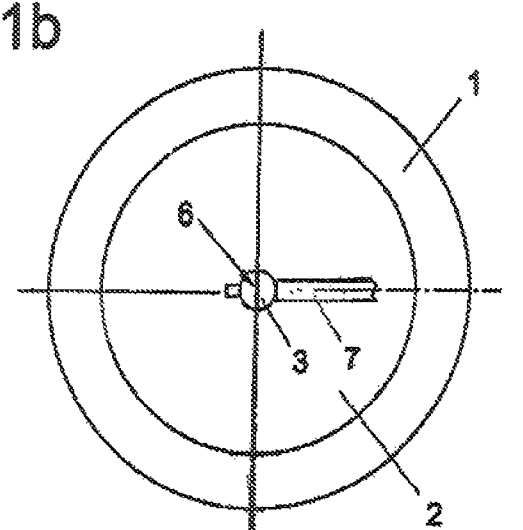
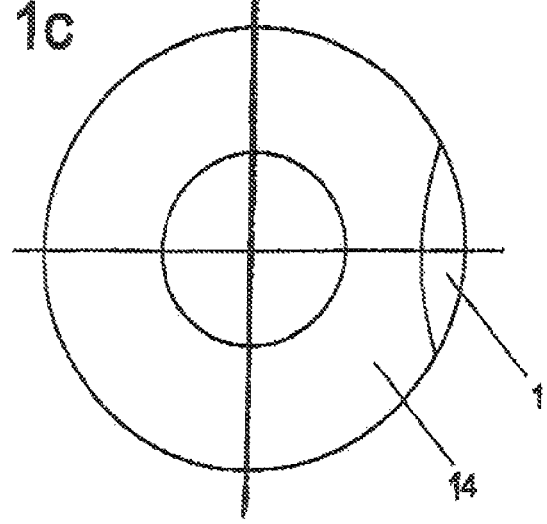

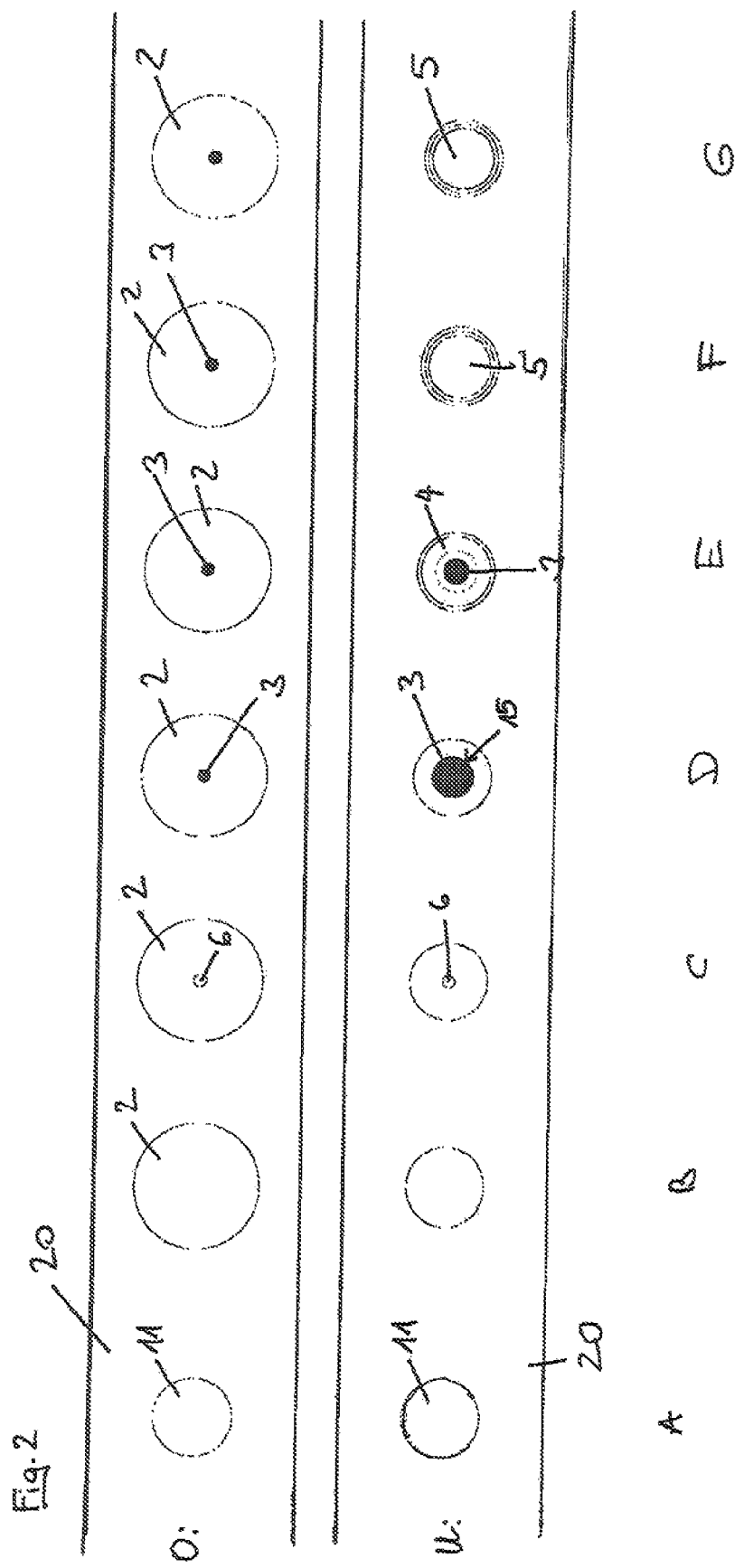

MEDICAL ELECTRODE

CROSS REFERENCE TO RELATED APPLICATIONS

This application claims priority from Austrian Application No. A 1542/2006, filed Sep. 15, 2006, is incorporated herein by reference.

BRIEF SUMMARY

The invention relates to a medical electrode for placing on the skin of a patient, having a support for attaching to the skin and a holding element for at least one electrically conducting connection piece, wherein the connection piece is covered on the skin side with an electrically conducting gel—in particular in a sponge. The invention also pertains to a process for producing a medical electrode.

BACKGROUND OF THE INVENTION

In the prior art, known medical electrodes (for example ECG electrodes) for adhering to the skin of a patient consist of a support layer one side of which adheres to the skin with a recess which usually has inserted therein an electrically conducting gel (in particular embedded in a sponge). (The description "patient" naturally refers here to both males and females). The gel is in electrically conducting contact with an electrically conducting connection piece which is also often described as a sensor element or eyelet.

The connection piece can, for example, consist of a discoid base with an approximately cylindrical projection. The projection projects through a recess in the holding element while the base is bonded to the holding element. At the cylindrical projection, the connection piece is connected with an electrical conductor, for example a cable, to transmit signals from or to the electrode via an electrocardiograph, for example. One side (the side of the discoid base facing the skin) of the sensor element is in direct contact with the gel and the opposite side, i.e. the side facing away from the skin, is fixed to the holding element. The holding element can, for example, be a label and be fixed to the support.

The disadvantage with the prior art is that on bedding in the medical electrode, the electrically conducting gel between the connection piece and the holding element diffuses and thus releases the connection (for example adhesive) between the two. This deleteriously affects the function and accuracy of the electrode; under some conditions the electrode becomes completely unusable.

Thus, the aim of the present invention is to improve a medical electrode of the type defined above to improve its durability. Further, its mechanical tolerance of further operations or use is to be improved.

This aim is achieved by the features of the independent claims. The gap between the holding element and the electrically conducting connection piece (i.e. the gap between the underside of the holding element and the electrically conducting connection piece) is closed by a sealing element which is preferably ring-shaped or is sealed by the sealing element, and so the electrically conducting gel can no longer diffuse into the gap between the holding element and the connection piece or the sensor element and thus no longer release the sensor element from the holding element.

Advantageously, the sealing element is a nonwoven which is impregnated with a heat-activatable adhesive. An example of a heat-activatable adhesive is a hot melt glue which can be activated by raising the temperature and on cooling and setting of the glue produces a solid and functional connection. Particularly in the case of stepwise operation, such a nonwoven impregnated with heat-activatable adhesive is advantageous (as will be described below in more detail), as such a heat-activatable adhesive can be heated up and thus made manipulatable a plurality of times.

The best results have been obtained when the sensor element is completely covered with a conducting surface, preferably Ag/AgCl; it is also preferable for the plastifiable base of the sensor element to contain ABS, and for the sensor element to contain carbon fibres in an amount of less than 30%, preferably about 20%.

In a cheaper alternative, the sealing element is a thermoplastic film which plasticizes on heating so that a seal is produced after the film sets on cooling.

BRIEF DESCRIPTION OF THE DRAWINGS

Further advantages and details of the invention will be described in more detail with the aid of the accompanying drawings. They show:

FIG. 1a: a cross section of an embodiment of a medical electrode of the invention;

FIG. 1b: a top view of an embodiment of a medical electrode of the invention;

FIG. 1c: a view from below of an embodiment of a medical electrode of the invention; and FIG. 2: diagrammatically shows steps in a process of the invention.

DETAILED DESCRIPTION

FIG. 1a shows an embodiment of a medical electrode of the invention in cross section. Said electrode consists of a support 1, in the present case formed from a foam. Said support 1 has a layer of adhesive 8 on the skin side so that the electrode can be adhered to the skin surface (not shown). The adhesive layer 8 should be skin tolerant so that no skin irritation occurs when adhered to the skin.

A holding element 2 can also be seen in the form of a label which is connected to the support 1 via a heat-activatable adhesive 9. Over a large area where the holding element 2 is located, the support 1 has a recess 11 in which an electrically conducting connection piece 3 (sensor element, eyelet) is pushed. A sponge 5 can also be seen, which contains an electrically conducting gel. The gel is in direct contact with the skin and passes signals to the sensor element 3 or vice versa. The sponge 5, electrical gel and sensor element 3 are all located in the recess 11 of the support 1 and are approximately flush with the underside of the support 1 (skin side), or as shown, the compressible sponge and electrical gel can project somewhat beyond the support 1 so that when stuck to the skin, the sponge is pressed flush with the recess 11. A tear-off film 14 protects the electrode on the skin side prior to use. For use, the tear-off film is removed. The sponge is also connected to the sensor element 3 via the heat-activatable adhesive 9. An approximately annular region on the sensor element 3 is covered with adhesive 9 and the sponge is placed on it after heating the adhesive 9. After the adhesive sets, the sponge is permanently attached to the electrode (or sensor element).

The external shape of the support 1 and recess 11 are in this case both approximately circular so that the support 1 forms a circular ring. However, the invention is not limited to this shape. As an example, oval or square external shapes may be envisaged for the support 1, as well as off-centre, non-circular recesses 11, etc. The shape of the recess 11 is essentially dependent on the application and the shape of the sensor element 3 or the shape of the sponge 5 which is inserted into the recess 11. The scope of the invention also clearly encompasses the support 1 and holding element 2 for the sensor element 3 being formed as one piece. The sensor element 3 has a base with which it is attached to the holding element 2, again via the heat-activatable adhesive 9. The holding element 2 also has a recess 6 through which the approximately cylindrical projection of the sensor element 3 projects. The electrical conductor 7 (multi-strand cable) is attached to this projection of the connection piece; in operation, it transmits signals to the electrocardiograph, not shown.

In the prior art, the electrically conducting gel can diffuse in the region of the gap 15 and loosen the heat-activatable adhesive. The gap 15 is between the side of the support turned towards the skin and the side of the connection piece 3 which faces this side but faces away from the skin surface. After a certain time at least, the gel enters the adhesive and deleteriously affects the connection between the connection piece 3 and the holding element 2. By using the ring-shaped seal element 4 of this case, formed by a nonwoven impregnated with heart-activatable adhesive, the electrically conducting gel cannot diffuse in. The gap is between the underside of the holding element 2 (i.e. the side of the holding element 2 which is directed towards the skin when stuck on or in use) and the electrically conducting connection piece 3. At this point it should be note that the positional information given refers to the normal positions shown in the Figures; the skin side is lowermost.

FIG. 1b shows a top view of the electrode of FIG. 1a. The support 1, holding element 2 and the cylindrical projection of the connection piece 3, from which the electrical conductor 7 leads, can be seen.

FIG. 1c shows a bottom view of the electrode; only the support 1 and sponge 5 with the electrically conducting gel can be seen. In this case, a transparent tear-off film 14 is arranged on the electrode to protect the electrode. A cut-out facilitates removal of the tear-off film 14.

The process of the invention will now be briefly described with reference to the implementation shown in FIG. 2. Letters A to H show the individual steps in the process; "O" denotes the view from above and "U" the view from below. A: In the first step, a recess 11 in the shape of a circular hole is stamped out of a strip 20 which forms the support 1. B: Over the recess 11, the round holding element 2 in the form of a label is bonded from the top onto the strip 20. C: In step 3, a circular recess 6 which is much smaller than the recess 11 is stamped out of the middle of the holding element 2. D: Next, in the fourth step, a sensor element 3 with its cylindrical projection is inserted into the recess 6; in the top view only the cylindrical projection can be seen and in the bottom view, only the base of the connection piece 3 can be seen. The cylindrical projection is pushed through the recess 6 E: In step 5, the vital step, the sealing element 4 in the form of a fixing ring is pushed concentrically from below over the sensor element 2. On heating, the sealing element 4 becomes attached to the holding element 2 and sensor element 3 and is sealed. F: Next, the sponge 5 is pushed over the connection piece into the recess and the sealing element and also sealed with the connection piece 3, again by heating, since the outer zone of the sensor element 3 has a heat-activatable adhesive which liquefies on heating and on cooling forms a stable connection with the sponge 5. Here, it is clearly advantageous if the sealing element 4 used is a nonwoven which is impregnated with heat-activatable adhesive as the adhesive can be activated several times simply by heating. In the present case, the nonwoven acts as both a seal and to attach the sponge 5. G: In step 7, the sponge 5 is filled with electrically conducting gel. H (not shown): Finally, a protective or covering film 14 is applied and then the electrode is stamped out.

What is claimed is:

1. A medical electrode for attaching to a skin surface of a patient, comprising,
   (a) a support adapted for attaching said medical electrode to the skin surface, said support having a recess therein,
   (b) at least one electrically conducting connection piece extending through said recess to electrically connect to an electrical conductor, said electrically conducting connection piece having a surface adapted for facing the skin surface, and an opposed surface contacting a holding element,
   (c) said holding element for holding said at least one electrically conducting connection piece, said holding element being connected to said support, said holding element having a side for facing the skin surface and contacting the connection piece, and further said holding element being heat-activatable adhesively affixed to said connection piece,
   (d) a sealing element positioned on the surface of the connection piece which is adapted for facing the skin surface and the side of the holding element which is adapted for facing the skin surface, thereby overlapping and sealing a contact area between said holding element and said connection piece, and
   (e) an electrically conducting gel applied to said surface of the connection piece which is adapted for facing towards the skin surface and the side of the holding element which is adapted for facing toward the skin surface.

2. An electrode according to claim 1, wherein the sealing element is a nonwoven material impregnated with a heat-activatable adhesive.

3. An electrode according to claim 1, wherein the sealing element is a nonwoven material.

4. An electrode according to claim 1, wherein said electrically conducting gel is arranged in a sponge.

5. An electrode according to claim 1, wherein said sealing element is ring-like.

* * * * *